US006967181B2

(12) United States Patent
Müller et al.

(10) Patent No.: US 6,967,181 B2
(45) Date of Patent: Nov. 22, 2005

(54) PRODUCTION OF A ZEOLITE-CONTAINING SOLID

(75) Inventors: Ulrich Müller, Neustadt (DE); Hartwig Voss, Frankenthal (DE); Erich Schubert, Bad Dürkheim (DE); Friedrich Hill, Meckenheim (DE); Hermann Petersen, Grünstadt (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/301,607

(22) Filed: Nov. 22, 2002

(65) Prior Publication Data

US 2004/0014591 A1 Jan. 22, 2004

(30) Foreign Application Priority Data

Jul. 17, 2002 (DE) .......................................... 102 32 406

(51) Int. Cl.⁷ ................................................ B01J 29/06
(52) U.S. Cl. ............................................. 502/64; 502/60
(58) Field of Search ..................... 502/60, 64; 549/531, 549/533, 523; 564/253, 267; 568/771

(56) References Cited

U.S. PATENT DOCUMENTS

| 4,648,960 | A | * | 3/1987 | Poeppelmeier et al. ..... 208/138 |
|---|---|---|---|---|
| 4,701,428 | A | | 10/1987 | Bellussi et al. |
| 5,863,516 | A | * | 1/1999 | Otterstedt et al. .......... 423/700 |
| 5,919,721 | A | * | 7/1999 | Potter .......................... 502/64 |
| 6,106,803 | A | | 8/2000 | Hasenzahl et al. |
| 6,491,861 | B1 | | 12/2002 | Grosch et al. |
| 6,521,562 | B1 | * | 2/2003 | Clem et al. .................. 502/214 |
| 2004/0053772 | A1 | * | 3/2004 | Muller et al. ................. 502/60 |
| 2004/0054199 | A1 | * | 3/2004 | Muller et al. ............... 549/523 |

FOREIGN PATENT DOCUMENTS

| DE | 10232406 | * | 1/2004 |
|---|---|---|---|
| EP | 0 638 362 | | 3/2001 |
| WO | WO 98/55229 | | 12/1998 |

* cited by examiner

*Primary Examiner*—Christina Johnson
(74) *Attorney, Agent, or Firm*—Oblon, Spivak, McClelland, Maier & Neustadt, P.C.

(57) ABSTRACT

In a process for concentrating an at least partially crystalline solid containing at least one zeolite in a mixture comprising at least one auxiliary, for example a template compound, and said solid, the mixture is ultrafiltrated in a step (II) to divide the mixture into a retentate and a permeate, the solids content in the retentate being higher than that in the mixture and the solids content in the permeate being lower than that in the mixture. This procedure allows auxiliaries, in particular template compounds, present in the permeate to be recycled into a crystallizing step (I) upstream of step (II).

16 Claims, 1 Drawing Sheet

PRODUCTION OF A ZEOLITE-CONTAINING SOLID

BACKGROUND OF THE INVENTION

1. Field of the Invention

Figure 1:
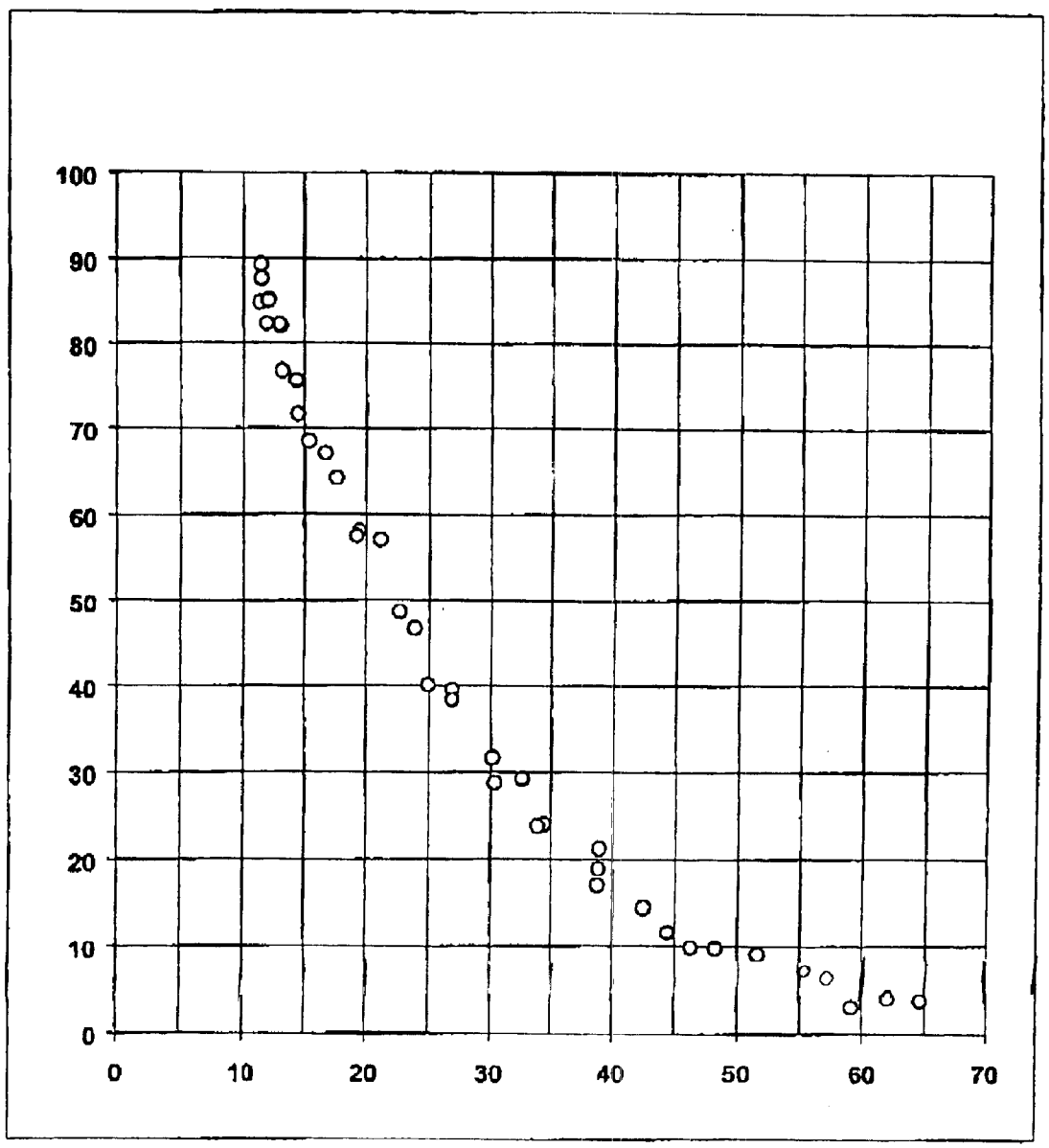

The present invention relates to a process for concentrating an at least partially crystalline solid containing at least one zeolite in a mixture comprising at least one auxiliary, for example a template compound, and said solid. In particular, the process comprises ultrafiltrating the mixture in a step (II) to divide the mixture into a retentate and a permeate, the solids content in the retentate being higher than that in the mixture and the solids content in the permeate being lower than that in the mixture. This process procedure allows auxiliaries, in particular template compounds, present in the permeate to be recycled into a crystallization step (I) upstream of step (II).

2. Description of the Background

Integrated processes for producing zeolite-containing shaped bodies are described, for example, in commonly assigned documents, in particular in WO 98/55229. This document focuses on the selection of the binder which allows compaction of the zeolite-containing solid to produce a shaped body. WO 98/55229 does not disclose any processes for concentrating the solid present in the mother liquor which are not covered by the conventional processes of filtration and/or centrifugation.

U.S. Pat. No. 6,106,803 describes a process for preparing titanium silicalite granulates comprising crystallizing a synthesis gel (=synthesis mixture; Si and Ti source, templating agent, base and water) under hydrothermal conditions, thereby producing a zeolitic suspension, and subjecting said suspension to spray-drying or fluidized-bed spray granulation drying after optionally concentrating and/or adding further substances. The solids content in the mixture prior to the spray drying step is in the range near 10%. Such a comparatively low solids content eventually leads to an unnecessarily reduced catalytic activity per unit mass in the shaped body, in particular when additives are added to the mixture for granulating.

EP-B 0 638 362 relates, inter alia, to a method for preparing a titanium silicalite catalyst, and here in particular the agglomeration of the primary particles, i.e. the microparticles which form during the crystallization step of the titanium silicalite synthesis. This agglomeration is achieved by reducing the pH of the solution containing the primary particles (zeolitic suspension) to values ranging from pH 5 to pH 10. The agglomeration forms part of an integrated process in which (i) firstly, the primary particles are prepared from a synthesis mixture of the prior art, (ii) subsequently, the secondary particles are agglomerated as mentioned above by reducing the pH, and (iii) the secondary particles are finally calcined. However, with respect to concentrating primary or secondary particles prior to agglomeration and/or recovering components of the mother liquor, EP-B 0 638 362 does not offer any teaching beyond that of the prior art.

U.S. Pat. No. 4,701,428 likewise addresses the problem of agglomeration in a mixture containing zeolitic microcrystals (here: smaller than 5 μm). The problem is solved by a special procedure for agglomerating titanium silicalite. This procedure comprises adding titanium silicalite crystals to a solution containing tetraalkyl orthosilicates at defined temperatures and quick drying. This document likewise does not offer any teaching beyond that of the prior art with respect to concentrating titanium silicalite crystals and/or recovering components of the mother liquor. A similar process is described in EP-B 1 106 576.

SUMMARY OF THE INVENTION

It is an object of the present invention to provide a process for concentrating the mixture which results from the at least partial crystallization of a synthesis mixture and contains at least one auxiliary, for example a template compound in a mother liquor, and an at least partially crystalline proportion of solids (containing at least one zeolitic material). In this process, the solids content in the mixture is to be increased, at the same time optionally separating at least part of the template-containing mother liquor from the solid. A higher solids content eventually leads to a higher catalyst activity per unit mass.

The process should also allow simplification of the integrated process for producing zeolite-containing shaped bodies as a whole, e.g. by omitting intermediate calcining steps. The process should furthermore lead to minimization of the consumption of potentially expensive or environmentally harmful chemicals, such as templating agents.

We have found that this object is achieved by ultrafiltrating, after step (I), the mixture (I) comprising at least one auxiliary and the at least partially crystalline zeolite-containing solid in a step (II) to divide the mixture into a retentate and a permeate, i.e. to concentrate it, the solids content in the retentate being higher than that in the mixture (I) originating from step (I) and the solids content in the permeate being lower than that in said mixture. This procedure allows auxiliaries, in particular template compounds, present in the permeate to be recycled into the abovementioned crystallization step (I).

DETAILED DESCRIPTION OF THE PREFERRED EMBODIMENTS

The solid described in the present invention can be compacted in a further step to produce a shaped body which may be used in particular as a catalyst for the epoxidation of organic compounds.

The process of the invention can also form part of an integrated process, namely a process for preparing an abrasion-resistant shaped body which contains at least one zeolitic material. Such a process can be subdivided in a purely schematic manner into the following steps:

step (I): at least partial crystallization of a solid containing at least one zeolite from a synthesis mixture to produce the mixture (I) comprising at least said solid and at least one auxiliary;

step (II): concentrating the solid present in the mixture (I) by ultrafiltration to produce a retentate and a permeate; this step optionally includes a solid/liquid separation, for example of the solid from the mother liquor;

step (III): agglomerating or granulating or agglomerating and granulating the solid particles in the concentrated retentate from step (II); this step optionally includes drying the solid particles;

step (S): shaping subsequent to step (II) or (III);

step (C): calcining subsequent to step (III) or (S);

the steps (S) and (C) being optional in each case.

The present text discusses the zeolite-containing solid of the invention and the shaped body obtainable therefrom in the context of applications in catalysis. However, this is not to be understood as meaning that the solid and/or shaped body cannot be used in other applications or contexts.

The present invention therefore provides a process for concentrating an at least partially crystalline solid containing at least one zeolite from a mixture comprising at least one auxiliary and said solid, which comprises ultrafiltrating the mixture in a step (II) to divide the mixture into a retentate and a permeate, the solids content in the retentate being higher than that in the mixture and the solids content in the permeate being lower than that in the mixture.

Essential expressions as used in the context of the present invention will now be defined.

For the purposes of the present invention, a "synthesis mixture" is any mixture from which a solid suspended in a mixture, preferably a mother liquor, can be obtained by crystallization, where the solid (i) should be at least partially crystalline and (ii) should contain at least one zeolitic material. The synthesis mixture can be a a sol, a gel, a solution or a suspension.

"Zeolites" are crystalline aluminosilicates having ordered channel and cage structures which have micropores. The term "micropores" as used in the present invention corresponds to the definition given in "Pure Appl. Chem." 45, p. 71ff., in particular p. 79 (1976), and refers to pores having a diameter of less than 2 mn. The network of such zeolites is composed of $SiO_4$ and $AlO_4$ tetrahedra which are linked via common oxygen bridges. An overview of the known structures is given, for example, by W. M. Meier and D. H. Olson in "Atlas of Zeolite Structure Types", Elsevier, $4^{th}$ Edition, London 1996. In addition to micropores, the solids of the invention which contain at least one zeolite can also have mesopores and/or macropores.

For the purposes of the present invention, a "solid", as present for example after the crystallization from the synthesis mixture, is any non-molecular material which (i) contains at least one zeolitic material and (ii) differs as a phase from the mixture (i) such that it can be subjected to a separation and/or concentration process. The solid is typically present in the form of particles suspended in a mother liquor, the particle size being given by that size of the particles which can just about still be collected by the membrane filter used in the process of the invention (during ultrafiltration or diafiltration). The size of the particles still to be regarded as a solid shall be at least 2 nm. A solid can be present as "primary particle" (after crystallization) or as "secondary particle" (after an agglomeration and/or granulation step).

For the purposes of the present invention, a "mother liquor" is any liquid phase which may contain any substance in dissolved form, but is free from particles of more than 2 nm in size. Here, the mother liquor may contain up to 5% by weight of particles of more than 2 nm in size. For the purposes of the present invention, the mother liquor may contain unreacted components of the synthesis mixture, i.e. auxiliaries, for example at least one compound which was used as a templating agent for the synthesis of the zeolite-containing solid in step (I). For the purposes of the present invention, a mother liquor is present only after completion of step (I), i.e. typically in connection with a suspension which contains solid particles of the above-defined type. In step (II), the permeate essentially consists of mother liquor.

For the purposes of the present invention, a "templating agent" is any substance as a result of which the solid which is formed during generation of the at least one zeolitic material from the synthesis mixture has at least one type of pore (micropores, mesopores, macropores). Typically nitrogenous organic bases are employed, which is to be understood as an illustrative example and not as a limitation.

Step (II) of the present invention concerns "concentrating" the solid-containing mixture from step (I). For the purposes of the present invention, "concentrating" means any step at the end of which a mixture is obtained in which the solids content is increased compared to the mixture originally employed. The mixtures may be suspensions of the solid but this does not have to be the case. "Separating" the solid from the mixture or from the suspension is explicitly included as a particular case in the definition of "concentrating".

For the purposes of the present invention, a "shaped body" is any three-dimensional body which has been produced in a shaping step (S) as described further hereinbelow. The shaped body is typically obtained by compacting a solid. This solid is in turn obtainable from step (II) and/or (III) with optional calcination (C).

"Ultrafiltration" as used in the present invention is a convective process in which particles (particles, macromolecules, etc.) and solvent(s) are separated primarily owing to particle size (and where the charge of the particles has little effect). A pressure gradient is applied across a typically anisotropic, semipermeable membrane. The smaller the pore size of the membrane, the larger the energy input, determined by the pressure gradient to be applied, necessary to effect the concentration. Microfiltration processes, i.e. filtration ultilizing membranes having a pore diameter in the micrometer range, are explicity included in the ultrafiltration method of the invention as long as they are distinguished from conventional cake filtration as defined hereinbelow.

There is no difference in principle between "diafiltration" and ultrafiltration, in particular the former likewise utilizes the membranes described further hereinbelow with the pore sizes specified there. In contrast to ultrafiltration, diafiltration is characterized by a different procedure, namely by the fact that the permeate (see definition hereinbelow) is continuously or partially replaced by water or another solution. This is then a purification step which for the purposes of the present invention can optionally be carried out subsequent to a concentration step i.e. ultrafiltration.

For the purposes of the present invention, ultrafiltration involves using membranes having pore sizes of from 1 nm to 1 $\mu$m. Therefore the type of filtration claimed herein for the purpose of concentrating, i.e. increasing the solids content, clearly differs from the prior art which is given by cake filtration and centrifugation of the zeolite-containing mixture. The separation/concentration achievable with these methods is effective only for solid particles of more than 10 $\mu$m in size.

The ultrafiltration or diafiltration separates the mixture originally employed into two phases which are different from each other, i.e. separable: permeate and retentate. For the purposes of the present invention, a "permeate" is that part of the mixture remaining after step (II) that is removed at the back of the membrane, i.e. the lower-pressure side (in conventional filtration, this would be the "filtrate"). Correspondingly, the "retentate" is formed on that side of the membrane which is exposed to the higher pressure and in which the solid particles which cannot pass through the pores of the membrane are concentrated.

The terms "granulation" and "agglomeration" as used in the present invention are considered to be synonymous and denote any conceivable process by which the diameter of a particle can be increased. The increase can occur by caking of particles or by growing on of further layers. Granulation encompasses, but is not limited to, processes which involve wetting the particles with at least one liquid. Furthermore it is possible, but not absolutely necessary, to add binders which promote or enable agglomeration or granulation.

A description of the individual steps of the integrated process for producing a shaped body containing at least one zeolitic material and the associated embodiments is given hereinbelow. Of particular importance is the novel process of the present application which essentially corresponds to step (II). As already mentioned above, the integrated process can be subdivided in a purely schematic manner into the following substeps:

step (I): at least partial crystallization of a solid containing at least one zeolite from a synthesis mixture to produce the mixture (I) comprising at least said solid and at least one auxiliary;

step (II): concentrating the solid present in the mixture (I) by ultrafiltration to produce a retentate and a permeate this step optionally includes a solid/liquid separation, for example of the solid from the mother liquor;

step (III): agglomerating or granulating or agglomerating and granulating the solid particles in the concentrated retentate from step (II); this step optionally includes drying the solid particles;

step (S): shaping subsequent to step (II) or (III);

step (C): calcining subsequent to step (III) or (S).

Step (I): Synthesis Mixture

There are no restrictions with regard to the at least one zeolite which is to be present in the solid or shaped body of the invention. Perference is given to using a titanium-, zirconium-, chromium-, niobium-, iron-, boron- or vanadium-containing zeolite, in particular a titanium silicalite.

Such titanium zeolites, in particular those having a crystal structure of the MFI type, and possibilities for their preparation are described, for example, in WO 98/55228, WO 98/03394, WO 98/03395, EP-A 0 311 983 or EP-A 0 405 978, the scope of which in this context is hereby fully incorporated in the context of the present application. Apart from silicon and titanium, such materials may also contain additional elements, for example aluminum, zirconium, tin, iron, cobalt, nickel, gallium, boron or small amounts of fluorine. In the zeolite catalysts preferably regenerated by the process of the invention, some or all of the titanium of the zeolite can be replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is usually from 0.01:1 to 0.1:1.

Titanium zeolites having the MFI structure are known to be identifiable from a particular pattern in their X-ray diffraction diagrams and, in addition, by a skeletal vibration band in the infrared (IR) at about 960 cm$^{-1}$, and thus differ from alkali metal titanates or crystalline and amorphous $TiO_2$ phases.

Said titanium, zirconium, chromium, niobium, iron and vanadium zeolites are usually prepared by reacting an aqueous mixture of an $SiO_2$ source, of a titanium, zirconium, chromium, niobium, iron or vanadium source, eg. titanium dioxide or an appropriate vanadium oxide, zirconium alkoxide, chromium oxide, niobium oxide or iron oxide, and of a nitrogenous organic base template, eg. tetrapropylammonium hydroxide, with or without adding basic compounds, in a pressure vessel at elevated temperature for several hours or a few days, resulting in an at least partially crystalline product. In the present invention, this step of the integrated process for producing a zeolite-containing shaped body is referred to as step (I).

In a preferred embodiment, step (I) involves using at least one template compound which is preferably employed, inter alia, to generate the desired pore size. In principle, there are no restrictions with regard to the template compound apart from the fact that they must contribute to pore formation. Examples of suitable template compounds include tetrapropylammonium hydroxide, tetrapropylammonium bromide, tetraethylammonium hydroxide, tetraethylammonium bromide or diamines or further template compounds known from the literature.

In a more preferred embodiment, the at least one zeolitic material obtained is a zeolite selected form the group consisting of titanium-, germanium-, tellurium-, vanadium-, chromium-, niobium- and zirconium-containing zeolites having a Pentasil zeolite structure, in particular the types assigned by X-ray analysis to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG or ZON structure and to mixed structures comprising two or more of the abovementioned structures. Titanium-containing zeolites having the ITQ-4, SSZ-24, TTM-1, UTD-1, CIT-1 or CIT-5 structure are furthermore possible for use in the process of the invention. Further titanium-containing zeolites which may be mentioned are those with the structure of ZSM-48 or ZSM-12.

Titanium zeolites having the MFI or MEL structure or MFI/MEL mixed structure are preferably used in the present invention. Specifically, the titanium-containing zeolite catalysts which are generally referred to as TS-1, TS-2 and TS-3, and titanium zeolites having a skeletal structure isomorphous to β-zeolite, are furthermore preferred.

Step (II): Ultrafiltration

In the processes of the prior art, the mixture which is obtained by the hydrothermal reaction in step (I) and which is typically a suspension of at least partially crystalline zeolite-containing solid in a mother liquor, is subsequently separated by filtration, centrifuged, spray-dried or spray-granulated according to conventional methods.

In the process of the invention, an ultrafiltration step (II) to concentrate and thus to increase the solids content is carried out subsequent to step (I) and prior to the agglomeration granulation step (III). In contrast to the prior art, this concentration is carried out without considerable granulation/agglomeration.

Ultrafiltration and diafiltration are convective processes in which solid particles are separated or concentrated primarily owing to particle size. A pressure gradient is applied across a porous membrane. The smaller the pore size of the membrane, the larger the energy input, determined by the pressure gradient to be applied, necessary to effect the separation. Here, the choice of membrane is of particular importance, as discussed hereinbelow.

In step (II) the mixture from step (I), i.e. usually a suspension, is divided into a retentate and a permeate, the solids content in the retentate being higher than that in the mixture and the solids content in the permeate being lower than that in the mixture. In a preferred embodiment, the solids content in the retentate at the end of step (II), i.e. after at least one pass of ultrafiltration or diafiltration, is from 20% to 80%, the solids content prior to step (II) being from 1% to 20%. In a particularly preferred embodiment, the solids content in the mixture prior to step (II) is from 1 to 20% by weight, and the solids content in the retentate subsequent to step (II) is from 50 to 80% by weight. The weight percentages are in each case based on the total weight of the mixture or the retentate, respectively.

The solids content in the permeate should not exceed 5% by weight, in a preferred embodiment it should not exceed one % by weight, in each case based on the total weight of the permeate. In a more preferred embodiment, the solids content in the permeate is so low that the permeate is optically clear (i.e. when observed using light of wavelengths ranging from 400 nm to 800 nm) or that the solids content cannot be detected by drying.

To avoid appreciable build-up of a covering layer ("secondary membrane") of the zeolite-containing solid on the surface of the membrane, which would lead to a significant decrease in the permeate flux, a relative velocity between membrane and suspension of 0.1–10 m/s is generated by pumped circulation, mechanical movement of the membrane or stirrers between the membranes.

Concentration can be achieved in a batch mode by passing the suspension a number of times through the membrane modules or continuously by means of a single pass through one or more feed and bleed stages connected in series. Furthermore, at least two membranes or membrane modules can be connected in series or in parallel.

The membrane process utilizes membrane separating layers having pore diameters between 1 nm (molecular cutoff limits of about 1 kD) and 1 $\mu$m, preferably from 10 nm (molecular cutoff limits of about 20 kD) to 500 nm. Particular preference is given to pore diameters of 50 nm to 200 nm. The separating layers can consist of at least one material selected from the group consisting of organic polymers, in particular cellulose derivatives, regenerated cellulose, polyolefins, polycarbonates, polysulfones, polymers having N—C bonds in the backbone; ceramics, in particular silicates, aluminas; glasses; metals, in particular ferrous metals and especially stainless steel materials; modifications of carbon, in particular materials obtained by pyrolysis of carbon percursor compounds, and combinations or mixtures of at least two of the abovementioned materials.

Furthermore, all materials which constitute the membrane must be practically inert and stable in the feed medium, i.e. in the present case in the above-described synthesis mixture. For mechanical reasons, the separating layers are usually applied to one or more single-layer or multilayer substrate layers made of the same material as the material of the separation layer or of different materials than the separating layer. Examples of possible combinations of materials are given in the table below:

| Separating layer | Substrate (coarser than separation layer) |
|---|---|
| Metal | Metal |
| Ceramic | Metal, ceramic or carbon |
| Polymer | Polymer, metal, ceramic or ceramic on metal |
| Carbon | Carbon, metal or ceramic |

Ceramic: e.g. $\alpha$-$Al_2O_3$, $ZrO_2$, $TiO_2$, SiC, mixed ceramic materials
Polymer: e.g. PP, PTFE, PVDF, polysulfone, polyethersulfone, polyetheretherketone, polyamide The membranes can be used in any geoemtry known to the person skilled in the art. Preference is given to flat, plate, tubular, coil, multichannel-element, capillary or wound geometries. It is essential that the chosen geometry is suitable for the corresponding pressure housing which allows separation between the retentate (rich in zeolite) and the permeate (low-zeolite or zeolite-free filtrate).

Optimum transmembrane pressures between retentate and permeate are dependent essentially on the diameter of the membrane pores, the hydrodynamic conditions influencing the build-up of the covering layer, and the mechanical stability of the membrane at the filtration temperature. These pressures are, depending on the membrane type, between 0.2 and 60 bar and preferably between 0.5 and 20 bar. Higher transmembrane pressures usually lead to higher permeate fluxes. When a number of modules is connected in series, the transmembrane pressure for each module can be reduced and thus adjusted by increasing the permeate pressure.

The operating temperature (filter temperature) depends on the membrane stability and the temperature stability of the synthesis mixture. The temperature is preferably between room temperature and 150° C., taking care that the solvent present in the synthesis mixture does not evaporate to an unacceptable extent. Temperatures between 30° C. and 80° C. are particularly preferred.

Higher temperatures usually lead to higher permeate fluxes. The permeate fluxes which can be achieved are strongly dependent on the type of membrane and membrane geometry employed, the process conditions and the feed composition (essentially the zeolite concentration). The permeate fluxes are typically between 5 and 500 kg/m$^2$/h.

Examples of membranes which can be employed are:

| Manufacturer | Membrane | Cutoff limit (kD) Pore diameter (nm) |
|---|---|---|
| Atech | UF/$TiO_2$ on $\alpha$-$Al_2O_3$/1,2 | 20 kD |
| Innovations | UF/$ZrO_2$ on $Al_2O_3$/1,2 | 50 nm |
| GmbH | MF/$\alpha$-$Al_2O_3$ on $\alpha$-$Al_2O_3$/1,2 | 0.1; 0.2; 0.4; 0.8; 1.2 $\mu$m |
| Rhodia/ | MF/$ZrO_2$ or $TiO_2$ on ceramic/1,2 | 0.1; 0.2; 0.45; 0.8 $\mu$m |
| Orelis | UF/$ZrO_2$ or $TiO_2$ on ceramic/1,2 | 15, 50, 150; 300 kD |
|  | UF/$ZrO_2$—$TiO_2$ on carbon/1 | 50; 150; 300 kD |
|  | MF/$ZrO_2$—$TiO_2$ on carbon/1 | 0.14 $\mu$m |
| Graver Technologies | UF/$TiO_2$ on steel/1 | 100 nm |
| Bekaert | MF/metal on metal | 0.2–1 $\mu$m |
| NADIR Filtrations | UF/polyethersulfone or polysulfone/3 | 10–150 kD |
| GmbH | UF/polyethersulfone/1 | 40, 100 kD |
| Creavis | UF/$ZrO_2$ on $\alpha$-$Al_2O_3$ and metal/3 | 25, 80 nm |
| Osmonics/ | UF/polysulfone/3 | 40 nm |
| Desal | UF/PVDF/3 | 10 kD |
|  | MF/PVDF/3 | 300 nm |
| Schumacher | UF/$TiO_2$ or $ZrO_2$ on ceramic/1,2 | 5, 10 and 50 nm |
|  | MF/$\alpha$-$Al_2O_3$ on ceramic | 100 and 200 nm |

1: tubular membrane;
2: multichannel element;
3: flat membrane for rolled modules, bag modules, plate stack modules or special modules with agitated membranes or stirrers between the membranes Solid/Liquid Separation In a further optional step which typically follows the step of concentrating by ultrafiltration and forms part of the above-defined step (II), the solids content of the retentate suspension can be further increased by conventional processes. This can be achieved, for example, by separating the suspension obtained into a plurality of parts and then separating off the solid contained in one part by cake-forming filtration, centrifuging and other suitable methods.

The filter cake thus obtained or the sediment can then be suspended in the remaining part of the suspension, if necessary after a washing step.

Step (III): Agglomeration/Granulation

Subsequent to step (II) of concentrating and/or separating, the solid particles can be enlarged by any known agglomeration and/or granulation process. Explicitly included are drying process steps which typically lead to at least partial agglomeration/granulation and/or are carried out subsequent to the agglomeration/granulation step. Such processes are indicated in the following non-limiting, i.e. illustrative, list:

(i) spray drying;
(ii) fluidized-bed drying;
(iii) spray drying with integrated fluidized bed;
(iv) batchwise vacuum contact drying;
(v) belt drying;
(vi) fluidized-bed spray granulation drying;
(vii) continuous contact drying;
(viii) continuous paste mill drying;
(ix) microgranulation in a spray tower;
(x) agglomeration by addition of a binder;
(xi) agglomeration by changing the pH.

With regard to points (i) and (vi), the relevant content of DE-197 31 627 or U.S. Pat. No. 6,106,803 is hereby fully incorporated in the context of the present application. With regard to point (xi), the relevant content of EO 0 638 362 B1 is hereby fully incorporated in the context of the present application.

For all points (i) to (xi), at least one additive is added prior to, during or after, or prior to and after, or prior to and during, or during and after, or prior to, during and after the respective drying/granulating/agglomerating step. Such additives may be selected, for example, from the following group: binders, fillers, pore formers. With regard to the selection of these additives, the remarks made in the next but one section for shaping apply.

In a preferred embodiment, some or all of the agglomerate/granulate is returned to step (III).

Aftertreatment

In order to improve the catalytic behavior, step (II), step (III) or both, in each case optionally in combination with a drying and/or calcining step, it is possible to carry out a subseqeunt treatment by washing repeatedly with a solution of hydrogen peroxide and sulfuric acid after which the solid can be redried and subsequently baked (calcined). This can be followed by treatment with alkali metal compounds to convert the zeolite from the H form into the cation form. The resulting solid can then be processed into a shaped body as described below.

Step (S): Shaping

The process of the invention for producing a zeolite-containing shaped body starts from the concentrated, optionally agglomerated solid after step (II) or (III) or from a dried and optionally calcined and/or aftertreated agglomerated powder.

In each case, the shaping procedure comprises the formation of a plastically deformable material which contains at least one zeolite-containing solid and furthermore a binder, if required a pore former based on polymers dispersible, suspendable or emulsifiable in aqueous solvents, if required a mixture containing at least one alcohol and water, if required one or more organic viscosity enhancers and further additives known from the prior art.

The plastically deformable material obtained by thorough mixing, in particular kneading, of the above components is preferably shaped by extrusion and the shaped body obtained is subsequently dried and finally calcined.

Useful binders are in principle any substances which impart a stronger adhesion and/or cohesion between the particles to be bound, here the (pulverulent) solid, than the physisorption which is present anyway without the binder. Preferred binders are selected from the group consisting of orthosilicates, tetraalkoxysilanes, tetraalkoxytitanates, tetraalkoxyzirconates or a mixture of two or more thereof, preferably tetramethoxysilane, tetraethoxysilane, tetrapropoxysilane and tetrabutoxysilane, the corresponding tetraalkoxytitanium and tetraalkoxyzirconium compounds and trimethoxy-, triethoxy-, tripropoxy-derivatives, with tetramethoxysilane, tetraethoxysilane and silica sols being especially preferred. Further preferred binders are amphiphilic substances, i.e. molecules having a polar and a nonpolar component, and graphite.

Preferred binders used for producing the shaped bodies of the invention are aluminum-containing binders. Examples of these are in particular clay minerals and synthetic or natural aluminas, e.g. alpha-, beta-, gamma-, delta-, eta-, kappa-, chi- and theta-alumina, and their inorganic or organometallic precursor compounds, e.g. gibbsite, bayerite, boehmite, pseudoboehmite and trialkoxyaluminates, preferably aluminum triisopropylate.

These binders can be used either alone, as a mixture of two or more thereof or together with other binders used for zeolitic materials, e.g. the abovementioned substances and/or oxides of silicon, of boron, of phosphorus, of zirconium and/or of titanium. Specific examples in this context are in particular silica, it being possible to introduce the $Sio_2$ into the shaping step as silica sol or in the form of tetraalkoxysilanes, and clays, e.g. montmorillonites, kaolins, bentonites, halloysites, dickites, nacrites and ananxites.

The shaped body of the invention preferably contains up to about 80, particularly preferably from about 10 to about 75, in particular from about 25 to about 45% by weight of binder, based in each case on the total mass of the shaped body.

As can already be seen from the above, it is in any case possible to use mixtures of two or more of the abovementioned binders.

In the process of the invention, it is possible to add polymers for establishing a specific pore size, pore size distribution and pore volume, if this is desired, polymers dispersible, suspendable or emulsifiable in aqueous solvents being used according to the invention for this purpose.

The polymer is preferably selected from polymeric vinyl compounds, e.g. polystyrene, polyacrylates, polymethacrylates, polyolefins, polyamides and polyesters. These polymers are substantially removed from the shaped body again during calcination.

If present, the polymer content during the production of the shaped body is from about 5 to about 90, preferably from about 15 to about 75, in particular from about 25 to 55% by weight, based in each case on the amount of zeolite-containing solid in the mixture.

A pasting agent is furthermore used in the production of the shaped body of the invention.

All substances suitable for this purpose and known from the prior art can be used as pasting agents. These are preferably organic, in particular hydrophilic polymers, e.g. cellulose, starch, polyacrylates, polymethacrylates, polyvinyl alcohol, polyvinylpyrrolidone, polyisobutene and polytetrahydrofuran. These substances primarily promote the formation of a plastically deformable material during the kneading, shaping and drying steps by bridging the primary particles and furthermore ensure the mechanical stability of the shaped body during shaping and drying. These substances are removed from the shaped body again during calcination.

Amines or amine-like compounds, e.g. tetraalkylammonium compounds or aminoalcohols, and carbonate-containing substances, such as calcium carbonate, may be introduced as further additives. Such further additives are described in EP-A 0 389 041, EP-A 0 200 260 and WO 95/19222, the relevant content of which is hereby fully incorporated by reference in the context of the present application.

Instead of basic additives, it is also possible to use acidic additives. These may result in, inter alia, a faster reaction of the metal acid ester (=binder) with the zeolite-containing solid. Preference is given to organic acidic compounds which may be burnt off after the shaping step by calcination. Carboxylic acids, e.g. formic acid, are particularly preferred. Such acids also modify the surfaces of the present shaped bodies.

It is possible to use further additives and solvents which help to plastify the material to be shaped. Such solvents and additives are known to the person skilled in the art.

It is of course also possible to use mixtures of two or more of the abovementioned additives.

The order of addition of the components of the zeolite-containing material (mixture) is not critical. It is possible either to first add the binder, then the water-dispersible, water-emulsifiable or water-suspendable polymer, the organic viscosity enhancer and, if required, the additive and finally the pasting agent, or to interchange the order of the binder, polymer, organic viscosity enhancer and additives.

Following the addition of the binder to the zeolite-containing solid to which the organic viscosity enhancer may have been added, the usually (but not necessarily) pulverulent material is homogenized in a kneader or extruder for 10 to 180 minutes. This is generally done at from about 10° C. to the boiling point of the pasting agent and at atmospheric pressure or slight superatmospheric pressure. Subsequently, the remaining components are added, and the resulting mixture is kneaded until an extrudable, plastic material is formed.

For the purposes of the present invention, for the methods in the shaping step, preference is given to methods in which shaping is effected by extrusion in conventional extruders, for example to form extrudates having a diameter of typically from about 1 to about 10 mm, in particular from about 2 to about 5 mm. Such extruders are described, for example, in Ullman's "Enzyklopädie der Technischen Chemie", 4th Edition, Vol. 2, page 295ff, 1972.

In principle, however, all conventional kneading and shaping devices and methods, as generally known in great numbers from the prior art for the production of, for example, shaped bodies, can be used for the shaping. The following procedures may generally be distingiushed: (i) briquetting, i.e. mechanical compression of a pulverulent material with or without a binder and/or other materials, (ii) pelletizing, i.e. compacting of a wet oder wetted pulverulent material by circular/rotating movements, and (iii) sintering, i.e. the material to be compacted is subjected to a heat treatment.

Specifically, the shaping step (S) can be selected from the following group, the combination of at least two of these methodes being explicitly included: briquetting by stamping pressing, roll pressing, annular-roll pressing, binderless briquetting; pelletizing, melting, spinning methods, deposition, foaming, spray drying; baking in a shaft furnace, convection oven, travelling grate, rotary-tube oven, mulling.

Compacting can be carried out at atmospheric pressure or superatmospheric pressure, for example in a pressure range from 1 bar to several hundred bar. Compacting can furthermore be carried out at ambient temperature or a temperature above ambient temperature, for example in a temperature range from 20° C. to 300° C. If the shaping step comprises drying and/or baking, temperatures of up to 1500° C. are conceivable. Finally, compacting can take place in the ambient atmosphere or in a controlled atmosphere. Controlled atmospheres are, for example, protective gas atmospheres, reducing and/or oxidizing atmospheres.

Aftertreatment of the Shaped Body and Calcining:

After the end of the at least one shaping process, the shaped bodies obtained are dried at in general from about 30 to 140° C. (for from 1 to 20 hours, atmospheric pressure) and calcined at from 400 to about 800° C. (for from 3 to 10 hours, atmospheric pressure).

Of course, the strands or extrudates obtained can be comminuted. They are preferably comminuted to give granules or chips having a particle diameter of from 0.1 to 5 mm, in particular from 0.5 to 2 mm.

These granules or these chips and also shaped bodies produced by other methods contain virtually no finer fractions than those having a minimum particle diameter of about 0.1 mm.

The shaped bodies of the invention or the shaped bodies produced by the process of the invention have good mechanical stability in combination with improved activity and/or selectivity compared with corresponding shaped bodies of the prior art.

In addition to the above-described process for producing a zeolite-containing solid, the present invention also encompasses said soliditself, obtainable by a process which comprises at least the following steps:

In addition, the process optionally comprises the separation and calcination of the aggregated or granulated solid particles.

step (I): at least partial crystallization of a solid containing at least one zeolite from a synthesis mixture to produce the mixture (I) comprising at least said solid and at least one auxiliary;

step (II): concentrating the solid present in the mixture (I) by ultrafiltration to produce a retentate and a permeate; this step optionally includes a solid/liquid separation, for example of the solid from the mother liquor;

step (III): agglomerating or granulating or agglomerating and granulating the solid particles in the concentrated retentate from step (II); this step optionally includes drying the solid particles.

In addition, the process optionally comprises the separation and calcination of the aggregated or granulated solid particles.

The invention furthermore comprises a shaped body containing at least one zeolitic material and which is obtainable from the above-described solid by carrying out the following steps:

step (S): shaping subsequent to step (II) or (III);

step (C): calcining subsequent to step (III) or (S).

What was said above applies with regard to the substeps which can be used for shaping and the conditions under which the agglomerated or unagglomerated solid or the compacted solid can be calcined.

Finally, the present invention provides the use of the zeolite-containing solid produced by one of the above-described processes or the solid or shaped body itself as likewise described above. The solids or shaped bodies of the invention or the solids or shaped bodies produced according to the invention can in particular be used for the catalytic conversion of organic molecules. Reactions of this type are, for example, oxidations, in particular the epoxidation of compounds having at least one C—C multiple bond.

In a preferred embodiment, this relates to the epoxidation of olefins, e.g. the preparation of propylene oxide from propylene and $H_2O_2$, the hydroxylation of aromatics, e.g. the preparation of hydroquinone from phenol and $H_2O_2$ or the conversion of toluene into cresol, the conversion of alkanes into alcohols, aldehydes and acids. Furthermore, the present catalyst can be used for: isomerization reactions, for example the conversion of epoxides into aldehydes, and further reactions described in the literature and using zeolite-containing catalysts as described, for example, in W. H Ölderich, "Zeolites: Catalysts for the Synthesis of Organic Compounds", Elsevier, Stud. Surf. Sci. Catal. 49 (1989), p. 69 to 93 (Amsterdam), and in particular for possible oxidation reactions, by B. Notari in Stud. Surf. Sci. Catal. 37 (1987), 413 to 425.

The above-described solids or shaped bodies containing at least one zeolitic material are particularly suitable for the epoxidation of olefins having from 2 to 8 carbon atoms, more preferably of ethylene, propylene or butene, and in particular of propene to give the corresponding olefin oxides. Accordingly, the present invention relates in particular to the use of the zeolite-containing solid or shaped body described herein for the preparation of propylene oxide starting from propylene and hydrogen peroxide. Further details of the reaction regime are well known from the prior art. In this context, the following commonly assigned documents are hereby fully incorporated in the present application: WO 01/36094, WO 01/34298, WO 01/72729, WO 01/10855, WO 00/21945.

The present invention furthermore relates to the use of the shaped body of the invention or the shaped body produced according to the invention or of a mixture of two or more thereof for the hydroxylation of aromatic organic compounds, for conversion of alkanes into alcohols, ketones, aldehydes and acids, for the ammoximation of ketones and for the preparation of amine N-oxides.

EXAMPLE

The membrane used for the ultrafiltration according to step (II) was a ceramic one-channel tubular membrane from Atech Innovations GmbH having an external diameter of 10 mm, an internal diameter of 6 mm and a length of 750 mm. The actual filtering membrane made of $ZrO_2$ having a pore size of 50 nm is applied to the inside of the ceramic tube made of $\alpha$-$Al_2O_3$.

The synthesis solution contained about 6.9% by weight of zeolite and about 3.4% by weight of tetrapropylammonium hydroxide (details can be found in EP-B 0 991 469).

The membrane was inserted into a pump circulation consisting of a storage container, a pump, a heat exchanger, a pressure tube for the membrane and a pressure maintenance valve. Furthermore, a flow meter, a thermometer and a manometer were positioned upstream of the membrane, and a manometer was positioned downstream of the membrane.

The suspension to be concentrated was pumped through the inside of the tubular membrane, a substream passing through the membrane as permeate and being removed through the ceramic support material and being collected on a balance. The flow velocity of the suspension in the tubular membrane was adjusted to 5 m/s, the filtration temperature was adjusted to 60° C., and the transmembrane pressure was adjusted to 1 bar. The flux during the batch concentration was about 90 kg/m$^2$/h at the start and about 4 kg/m$^2$/h at the end, the zeolite content being 62.5% and the tetrapropylammonium hydroxide (TPA) content being 3.4%. The solids (zeolite and TPA) content was determined by drying or, for the TPA, by titration. The permeate was free from zeolite beyond the experimental limit of detection and contained tetrapropylammonium hydroxide in a concentration of about 3.4%.

FIG. 1: The total solids content (zeolite plus TPA; in % by weight) obtained with this experimental setup is plotted on the horizontal axis as a function of the permeate flux (in kg/m$^2$h) which is plotted on the vertical axis.

We claim:

1. A process for concentrating an at least partially crystalline solid containing at least one zeolite from a mixture comprising a mother liquor, at least one template compound and said solid, which comprises ultrafiltrating the mixture in a step (II) to divide the mixture into a retentate and a permeate, said permeate consisting essentially of the mother liquor,
   wherein the solids content in the mixture prior to step (II) is from 1 to 20% by weight, and in the retentate subsequent to step (II) is from 50 to 80% by weiaht, in each case based on the total weight of the mixture or the retentate, respectively,
   and wherein the solids content in the permeate does not exceed 1% by weiaht, based on the total weight of the permeate.

2. A process as claimed in claim 1, wherein at least one membrane used for the ultrafiltration and contains separating layers having pore diameters ranging from 10 nm to 500 nm.

3. A process as claimed in claim 2, wherein the geometry of the at least one membrane is selected from the group consisting of flat, tubular, multichannel-element, capillary and wound geometries.

4. A process as claimed in claim 1, wherein the transmembrane pressure ranges from 0.5 to 20 bar.

5. An integrated process for producing a solid containing at least one zeolite, which process comprises,
   (I) at least partially crystallizing a solid containing at least one zeolite from a synthesis mixture to produce a mixture (I) comprising at least said solid and at least one template compound;
   (II) concentrating the solid present in the mixture (I) by ultrafiltration to produce a retentate and a permeate, said permeate comprising the at least one template compound;
   (III) agglomerating or granulating or agglomerating and granulating the solid particles in the retentate from (II),
   wherein the permeate obtained in (II) or the at least one template compound present therein is at least partially recycled into (I).

6. A process as claimed in claim 5, wherein at least one of the steps of agglomerating or granulating or at least two of these steps is/are selected from the group consisting of:
   (i) spray drying
   (ii) fluidized-bed drying
   (iii) spray drying with integrated fluidized bed
   (iv) batchwise vacuum contact drying
   (v) belt drying
   (vi) fluidized-bed spray granulation drying
   (vii) continuous contact drying
   (viii) continuous paste mill drying (ix) microgranulation in a spray tower (x) agglomeration by addition of a binder (xi) agglomeration by changing the pH.

7. A process as claimed in claim 6, wherein, in steps (i) to (xi), at least one additive is added prior to, during or after the respective drying/granulating/agglomerating steps.

8. A process as claimed in claim 6, wherein, in steps (i) to (xi), at least one additive is added prior to and after the respective drying/granulating/agglomerating steps.

9. A process as claimed in claim 6, wherein, in steps (i) to (xi), at least one additive is added prior to and during the respective drying/granulating/agglomerating steps.

10. A process as claimed in claim 6, wherein, in steps (i) to (xi), at least one additive is added during and after the respective drying/granulating/agglomerating steps.

11. A process as claimed in claim 6, wherein, in steps (i) to (xi), at least one additive is added prior to, during and after the respective drying/granulating/agglomerating steps.

12. A process as claimed in claim 1, wherein step (II) is followed by a shaping step (S), the at least one shaping step being selected from the group consisting of briquetting, pelletizing and sintering.

13. A process as claimed in claim 5, wherein step (II) or step (III) is followed by a shaping step (S), the at least one shaping step being selected from the group consisting of briquetting, pelletizing and sintering.

14. A process as claimed in claim 1, wherein step (II) is followed by a calcining step (C) at temperatures in excess of 400 C.

15. A process as claimed in claim 5, wherein at least one of steps (II) and (III) is followed by a calcining step (C) at temperatures in excess of 400 C.

16. The process as claimed in claim 1, wherein the mother liquor does not contain more than 5% by weight of particles of more than 2 nm in size.

* * * * *